July 28, 1964 W. E. DUFFETT Plant Pat. 2,428
CHRYSANTHEMUM PLANT
Filed March 13, 1963
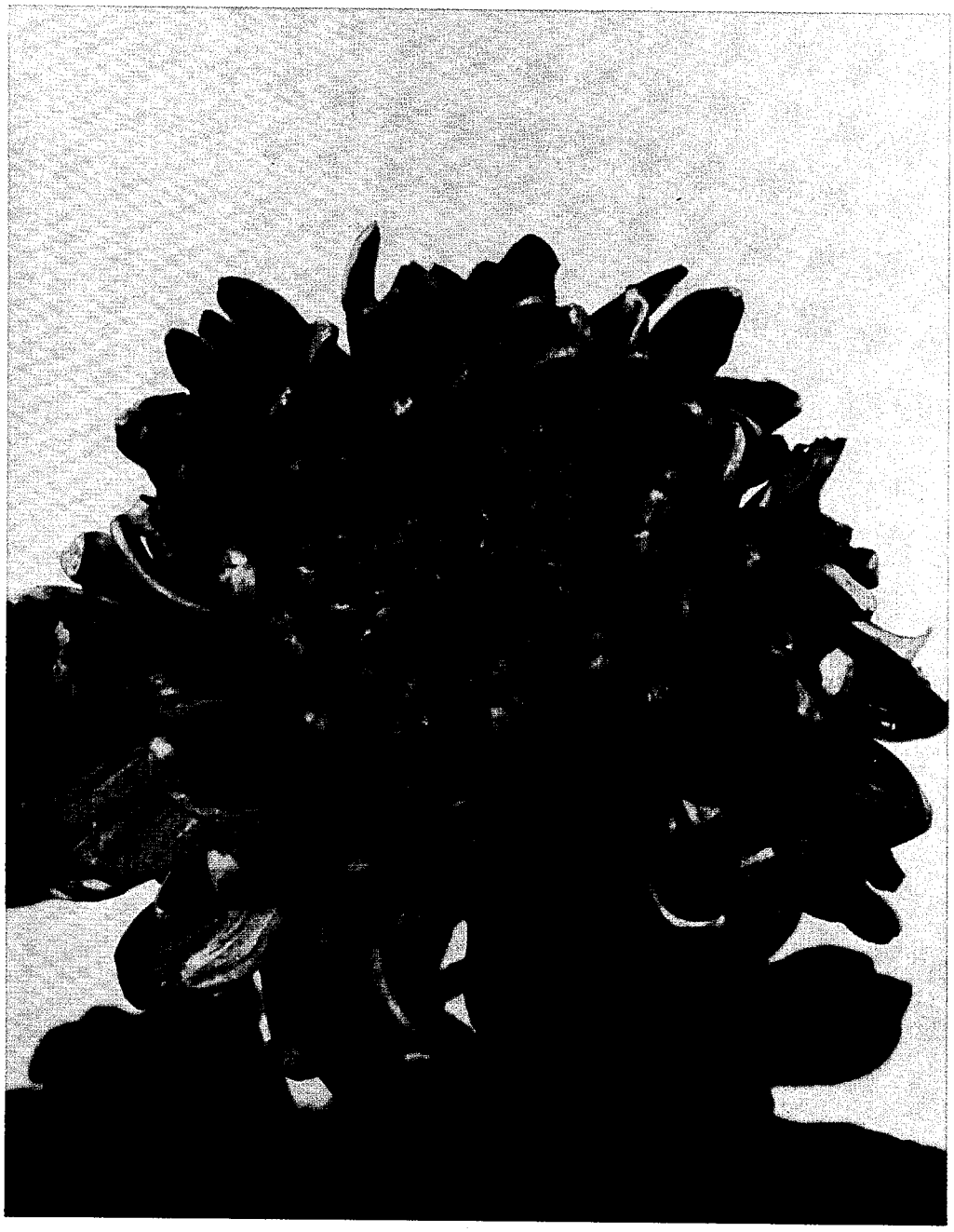
INVENTOR:
W. E. DUFFETT
by Robb & Robb
attorneys United States Patent Office Plant Pat. 2,428
Patented July 28, 1964

2,428
CHRYSANTHEMUM PLANT

William E. Duffett, Barberton, Ohio, assignor, by mesne assignments, to George J. Ball, Inc., West Chicago, Ill.

Filed Mar. 13, 1963, Ser. No. 264,991
1 Claim. (Cl. Plt.—82)

My present invention comprises a new and distinct variety of chrysanthemum plant which is a sport of the Harvest Giant Mum variety known as U.S. Patent No. 2,001.

The parent variety, U.S. Patent No. 2,001, was the result of a very intensive program of hybridization and cross-breeding, resulting in the said variety and particularly of course the crossing of that variety's parents "Attraction," an unpatented variety, with one designated as No. 5350 by the hybridizer thereof.

In the instant case, the sport has been discovered during the course of reproduction and growth of chrysanthemums on a production basis and while in different conditions somewhat, by reason of the fact that the instant variety was discovered at Barberton, Ohio whereas the parent variety originated in the vicinity of Niles, Michigan, nevertheless, the desirable characteristics of the parent variety are contained in the specific plant hereof, with the primary novel difference residing in the bronze-like color which the plant presents as a whole when viewed in a grouping or from a distance, this particular variety maintaining the characteristics of the parent, possessing the ability to respond well in a pot chrysanthemum program, the primary difference residing in the color as previously suggested.

The color as such is of a strong reddish-orange color as determined by appropriate reference to color charts, and more specifically, the blooms of my new variety are of a strong reddish-orange color (Nickerson Color Fan published by The Munsell Color Company). As grown in the vicinity of Barberton, Ohio, under uniform culture, plants of my new variety produce large flowers in a somewhat shorter growth habit than other varieties although quite similar in most aspects to the parent as before noted.

My new variety may be compared to other varieties found during the same course of hybridization, and specifically, U.S. Patent No. 2,003, but possessing a shorter growth habit than said U.S. Patent No. 2,003.

The instant variety is an improvement over a comparable variety, U.S. Patent No. 2,004, in that it flowers two to three weeks earlier than said U.S. Patent No. 2,004, chrysanthemum, and produces larger flowers likewise.

Under conditions of culture previously mentioned which have taken place in the vicinity of Barberton, Ohio, my new variety blooms very early and profusely, almost continuously and in the fall as is common with chrysanthemums. The buds of my new variety are large and may be characterized as somewhat globular; being affected by wet weather in that some rot is noted, and the hot weather delays flowering to some extent.

On the whole, the blooms of my new variety are large and when fully expanded reach a size of 6½ inches in diameter in many cases, being borne in clusters and the clusters somewhat pyramidal in general shape.

The stems are medium and strong, the flower when first open having a high center and tending to flatten as it ages.

Petalage as stated should be noted as being very double, with the number of petals under normal conditions being of such great number as being too many to count.

My new variety has been asexually reproduced by stem cuttings in the vicinity of Barberton, Ohio, and my new variety has been found to retain its distinctive characteristics through successive asexual reproductions.

The accompanying drawing forming a part hereof, shows a typical bloom of my new variety of chrysanthemum.

The following is a detailed description of my new variety of chrysanthemum plant, the color references being to the Nickerson Color Fan published by The Munsell Color Company:

Parentage: Sport. Sport of Plant Patent No. 2,001.
Classification: Botanic—*Chrysanthemum indicum.*

*Flower*

Blooming habit: Blooms profusely from early September until a killing frost. Observations were made in the vicinity of Barberton, Ohio in October.

Bud:

*Size.*—Large.

*Form.*—Globular.

Somewhat affected by rot in wet weather and hot weather delays flowering.

*Color.*—When sepals first divide—between 2.5R 4/10 moderate red and 2.5R 5/12 strong red. When petals begin to unfurl—between 2.5R 4/10 moderate red and 2.5R 5/12 strong red. When half blown: inside of petals—same as sepals; reverse of petals—between 5YR 8/7 light orange and 7.5YR 8/8 moderate orange yellow.

*Sepals.*—Smooth edge and curl back as bud opens.

*Calyx.*—Shape—apple. Size—larger and broad. Aspect—mossy.

*Peduncle.*—Medium, smooth, stiff and heavy, with bud opening well and somewhat affected by adverse conditions.

Bloom:

*Size.*—Very large. Average size when fully expanded—6½".

*Borne.*—Clusters and pyramidal shaped.

*Stems.*—Medium and strong.

*Form.*—When first open—high center, flattens as it ages.

*Petalage.*—Very double with too many petals to count under normal conditions.

*Color.*—Center of flower—between 5YR 8/7 light orange and 7.5YR 8/8 moderate orange yellow. Outer petals—between 2.5YR 4/10 moderate red and 2.5YR 5/12 strong red. Base of petals—2.5Y 9/9 brilliant yellow. Inside of petals—between 5R 6/11 deep yellowish-pink and 5R 5/13 vivid red. Reverse of petals—between 5YR 8/7 light orange and 7.5YR 8/8 moderate orange yellow. General tonality from a distance—between 10R 6/12 strong reddish-orange and 10R 5/11 strong reddish-orange.

*Discoloration.*—General tonality at end of: First week—between 10R 6/12 strong reddish-orange and 10R 5/11 strong reddish-orange. Second week—small proportion 10R 5/11 strong reddish-orange and a larger proportion 10R 6/12 strong reddish-orange. Third week—between 10R 7/9 strong yellowish pink and 10R 6/12 strong reddish-orange.

*Petals*

Texture: Thick and soft.
Appearance: Inside—satiny. Outside—satiny.
Form: Pointed.
Arrangement: Imbricated.
Persistence: Hang on and dry.
Fragrance: None.
Lastingness: On the plant—very long. As cut flowers—long.

*Genital Organs*

Stamens, anthers: small and many.
Arrangement: Mixed with petaloids.
Stamens, filaments: Long.
Styles: Loosely separated, of medium length and thin.
Ovaries: Some protruding from calyx.

*Plant*

Form: Bush.
Growth: Medium and compact.
Height: 18 inches.
Spread: 24 inches.

*Foliage*

Leaflets are found in pairs in a spiral arrangement upon the stem.
Size: Large.

Quantity: Normal.
Shape: Oval.
Texture: Glossy.
Ribs and veins: Light.
Edge: Undulated.
Serration: Small.
Stipules: Short and smooth.

I claim:

A new and distinct variety of chrysanthemum plant substantially as herein disclosed, characterized as to novelty by the strong reddish-orange color of its blooms, the very double arrangement of its petals, vigorous and compact habit of growth, abundant, large size of foliage and blooms, and very early, continuous and long blooming period.

No references cited.